United States Patent
Leng et al.

(10) Patent No.: US 11,541,605 B2
(45) Date of Patent: Jan. 3, 2023

(54) SYSTEMS AND METHODS FOR QUALITY CONTROL IN 3D PRINTING APPLICATIONS USING A 3D PRINTED PHANTOM

(71) Applicant: Mayo Foundation for Medical Education and Research, Rochester, MN (US)

(72) Inventors: Shuai Leng, Rochester, MN (US); Kiaran P. McGee, Rochester, MN (US); Jane M. Matsumoto, Rochester, MN (US); Joel L. Kuhlmann, Rochester, MN (US); Jonathan M. Morris, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 48 days.

(21) Appl. No.: 17/023,060

(22) Filed: Sep. 16, 2020

(65) Prior Publication Data
US 2020/0406559 A1 Dec. 31, 2020

Related U.S. Application Data (62) Division of application No. 15/779,411, filed as application No. PCT/US2016/063926 on Nov. 29, 2016, now Pat. No. 10,814,557.
(Continued)

(51) Int. Cl.
*B33Y 50/02* (2015.01)
*B29C 64/393* (2017.01)
(Continued)

(52) U.S. Cl.
CPC ............ *B29C 64/393* (2017.08); *A61B 6/032* (2013.01); *A61B 6/584* (2013.01); *B29C 64/30* (2017.08); *B33Y 30/00* (2014.12); *B33Y 40/20* (2020.01); *G01D 18/00* (2013.01); *G06F 3/1208* (2013.01); *G06F 3/1256* (2013.01); *G09B 23/286* (2013.01); *G16H 50/50* (2018.01);
(Continued)

(58) Field of Classification Search
CPC ...................... A61F 2002/30943; B33Y 50/02
USPC .......................................................... 700/98
See application file for complete search history.

(56) References Cited

U.S. PATENT DOCUMENTS 7,050,876 B1 * 5/2006 Fu ...................... G05B 19/4099
700/98
7,056,019 B1 6/2006 Hanson
(Continued)

FOREIGN PATENT DOCUMENTS

WO 2002030157 A2 4/2002

OTHER PUBLICATIONS

International Search Report and Written Opinion from parent PCT application No. PCT/US16/63926, dated Mar. 16, 2017, 15 pages.
(Continued)

*Primary Examiner* — Suresh Suryawanshi
(74) *Attorney, Agent, or Firm* — Quarles & Brady LLP (57) ABSTRACT

The present disclosure provides systems and methods for performing quality control assessments of a three dimensional (3D) printing system. In particular, the present disclosure provides a phantom designs for use in 3D printing systems, as well as methods of quality control for a 3D printing system performed using a 3D printed phantom.

13 Claims, 6 Drawing Sheets

Related U.S. Application Data (60) Provisional application No. 62/260,554, filed on Nov. 29, 2015.

(51) Int. Cl.

| | | |
|---|---|---|
| *A61B 6/03* | (2006.01) | |
| *G01D 18/00* | (2006.01) | |
| *G16H 50/50* | (2018.01) | |
| *B29C 64/30* | (2017.01) | |
| *G06F 3/12* | (2006.01) | |
| *B33Y 40/20* | (2020.01) | |
| *B33Y 30/00* | (2015.01) | |
| *A61B 6/00* | (2006.01) | |
| *G09B 23/28* | (2006.01) | |

(52) U.S. Cl.
CPC .............. *A61B 6/504* (2013.01); *A61B 6/505* (2013.01); *B33Y 50/02* (2014.12)

(56) References Cited

U.S. PATENT DOCUMENTS

| | | | |
|---|---|---|---|
| 7,328,080 B2* | 2/2008 | Fu ..................... | B33Y 80/00 700/98 |
| 7,330,026 B2 | 2/2008 | Wang | |
| 8,173,968 B1 | 5/2012 | Nelms | |
| 8,340,383 B2 | 12/2012 | Matsuura | |
| 2003/0074174 A1* | 4/2003 | Fu ..................... | H04R 25/658 703/13 |
| 2004/0062358 A1* | 4/2004 | Lang ..................... | A61B 6/505 378/207 |
| 2006/0027756 A1 | 2/2006 | Thomson | |
| 2009/0052755 A1 | 2/2009 | Herold | |
| 2010/0020200 A1 | 1/2010 | Fujiwara | |
| 2010/0202001 A1 | 8/2010 | Miller | |
| 2012/0012813 A1 | 1/2012 | Chen | |
| 2012/0128132 A1 | 5/2012 | Coolens | |
| 2012/0253180 A1 | 10/2012 | Emelianov | |
| 2013/0024231 A1 | 1/2013 | Gordon | |
| 2013/0242317 A1 | 9/2013 | Leavitt | |
| 2015/0016699 A1 | 1/2015 | Ritt | |
| 2015/0032142 A1 | 1/2015 | Silvestro | |
| 2015/0309149 A1 | 10/2015 | Holdsworth | |
| 2015/0321426 A1 | 11/2015 | Lee | |
| 2016/0041270 A1 | 2/2016 | Dai | |
| 2016/0191887 A1 | 6/2016 | Casas | |
| 2017/0370859 A1 | 12/2017 | Gay | |

OTHER PUBLICATIONS

European Patent Office, Extended European Search Report, Application No. 16869353.9, dated Jun. 27, 2019, 9 pages.

\* cited by examiner

SYSTEMS AND METHODS FOR QUALITY CONTROL IN 3D PRINTING APPLICATIONS USING A 3D PRINTED PHANTOM

CROSS-REFERENCES TO RELATED APPLICATIONS

The present application is divisional of U.S. patent application Ser. No. 15/779,411, filed on May 25, 2018, which is a National Stage Filing of PCT/US2016/063926, entitled "Systems and Methods for Quality Control in 3D Printing Applications," internationally filed on Nov. 29, 2016, which is based on, claims priority to, and incorporates herein by reference in its entirety, U.S. Provisional Patent Application No. 62/260,554, filed Nov. 29, 2015, and entitled "Systems and Methods for Quality Control in 3D Printing Applications."

STATEMENT REGARDING FEDERALLY SPONSORED RESEARCH

Not Applicable.

BACKGROUND

This disclosure relates generally to 3-dimensional (3D) printing and, more particularly, to systems and methods for quality control of a 3D printer.

As 3D printing technology has advanced, the medical field has begun experimenting with 3D printing to fabricate anatomic models for surgical planning, surgical guide, human body part replacements, including new bone scaffolds, hand replacements, and even organs. In order to be viable for human use, the printed parts must have a high degree of dimensional accuracy. 3D printers, like other manufacturing equipment, can fall out of calibration over time, causing the printing of parts that do not meet the required dimensional specifications. The 3D printing process comprises multiple steps, and has several possible sources of error that may affect the production of a part. As the printing of complex parts can take several hours to complete, it is important to reduce the amount of unacceptable parts. Thus, quality control (QC) is a valuable concept that has generally not been applied in 3D printing in a systematic and consistent fashion.

BRIEF SUMMARY

The present disclosure provides systems and methods for quality control for a 3D printing system and 3D printing process. For example, a 3D printed phantom and method of using the 3D printed phantom for quality control processes is provided. Using the phantom, an operator is able to test the geometric accuracy, resolution, and shape fidelity of outputted 3D printed parts. The procedure described herein allows an operator to identify potential errors at various points in the 3D printing process, from the scanning phase to inspection of the final 3D printed part.

In one aspect, the present disclosure provides a 3-dimensional (3D) phantom for performing a quality control assessment of a 3D printing system. The phantom includes a support base formed of a radiopaque material and provides at least one surface including a plane. The phantom further includes a plurality of positive features protruding from the plane and a plurality of negative features embedded into the base section. The positive features and the negative features, collectively, may include geometric objects and anatomic objects.

In another aspect, the present disclosure provides a method of quality control for a 3D printing system. The method includes scanning a 3D reference phantom with a scanning device thereby producing one or more scanned images of the 3D reference phantom. The method further includes importing the one or more scanned images into modeling software, and generating a 3D model of the 3D reference phantom in the modeling software. The method further includes printing a printed 3D phantom on a 3D printer in communication with the modeling software. The method further includes comparing a size of at least one geometric feature of the printed 3D phantom to a size of a corresponding at least one geometric feature of the 3D reference phantom and, upon comparing the size of the at least one geometric feature of the printed 3D phantom to the size of the corresponding at least one geometric feature of the 3D reference phantom, determining at least one of a geometric accuracy, a resolution, and a shape fidelity of the 3D printing system In yet another aspect the present disclosure provides method of producing a patient-specific phantom using a 3D printing system. The method includes scanning a portion of a patient's body with a scanning device thereby producing one or more images of the portion of the patient's body and importing the one or more images into modeling software. The method further includes segmenting the one or more images to form a segmented set of images, generating a 3D model of the portion of the patient's body from the segmented set of images, and printing, with a 3D printer, a printed 3D model of the portion of the patient's body. The method further includes scanning the printed 3D model of the portion of the patient's body with the scanning device thereby producing one or more images of the printed 3D model, registering the one or more images of the printed 3D model to the 3D model in the modeling software, and calculating a geometric difference between the one or more images of the printed 3D model and the 3D model in the modeling software on a point-by-point basis. The method further includes include determining if the calculated geometric difference between the one or more images of the printed 3D model and the 3D model in the modeling software are within a pre-determined tolerance.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The invention will be better understood and features, aspects and advantages other than those set forth above will become apparent when consideration is given to the following detailed description thereof. Such detailed description makes reference to the following drawings.

DETAILED DESCRIPTION

Currently, a need in the art exists for a method of quality control for 3D printed parts. As dimensional accuracy and shape fidelity are of the utmost importance, for example, in medical applications, it is imperative that parts created via 3D printing will meet the stringent requirements and have all dimensions fall within acceptable tolerances. For models involving patients, it is critical to have the models accurately represent patient anatomy and pathology. The immense cost and time associated with producing 3D printed parts requires that the production of unusable parts be limited as much as reasonably possible. Therefore, it would be desirable to have a phantom and associated methods of quality control for a 3D printing system.

Figure 1:
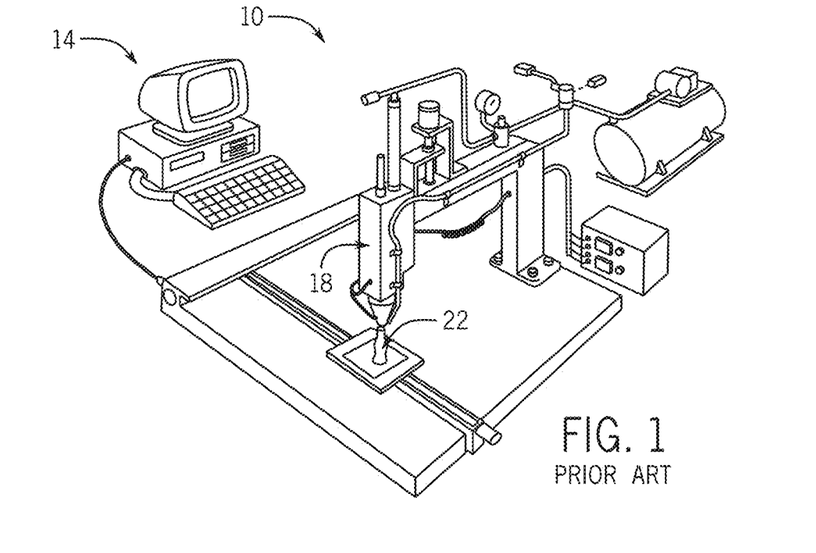
FIG. 1 is a perspective view of a prior-art 3D printing system.

FIG. 1 shows a prior art 3D printing system. The 3D printing system 10 can be used to produce parts that may be used, for example, in medical applications. The 3D printing system 10 includes a computer 14 and a printer 18. The computer 14 typically includes 3D modeling software to communicate data to the printer 18. The printer 18 receives the data from the modeling software and produces (i.e., 3D prints) a part 22 that was designed by a user with the modeling software.

It should be understood by one skilled in the art that many different models of 3D printers can be used to accomplish the 3D printing of parts that may be used in medical applications. One such model suitable for the production of parts to be used in the medical field is the MakerBot Replicator II printer, although many others are similarly acceptable.

Further, it should be understood that several types of 3D printing processes can be used to produce these parts. One type of 3D printing process that may be used is selective laser sintering (SLS); however, other 3D printing processes, such as stereolithography (SLA), fused deposition modeling (FDM), selective laser melting (SLM), electronic beam melting (EBM), laminated object manufacturing (LOM), as well as other 3D printing processes known in the art may be used to produce 3D printed parts for use in medical applications.

Figure 2:
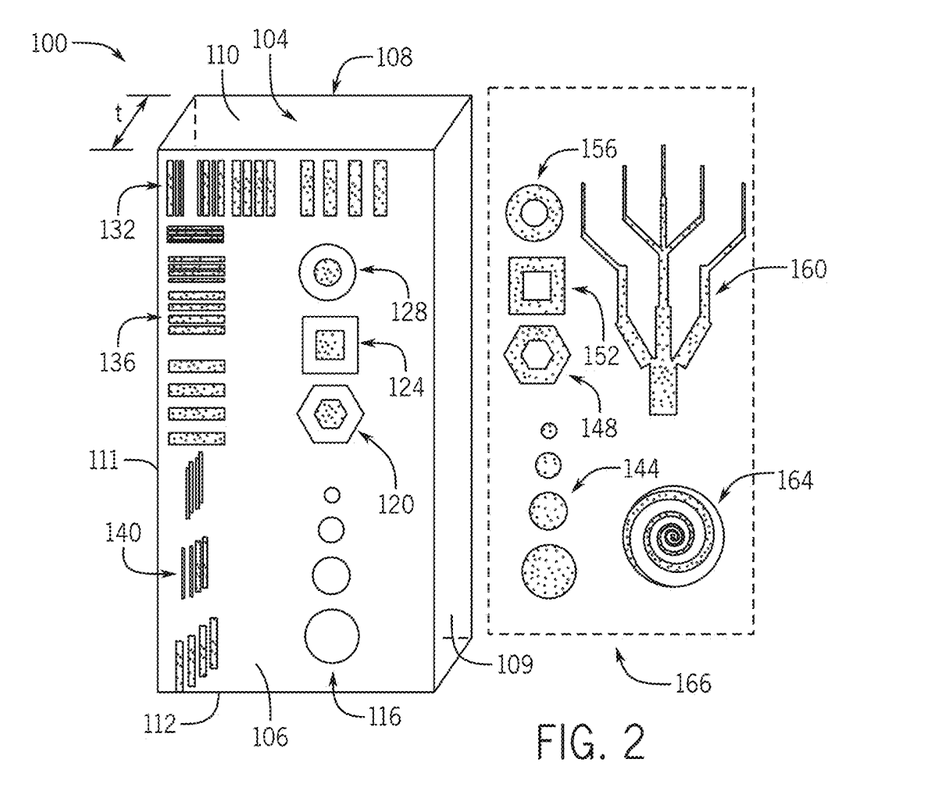
FIG. 2 is an illustration of a phantom for a 3D printing system in accordance with one aspect of the present disclosure.

FIG. 2 shows one non-limiting example of a 3D phantom 100 configured to be used for performing quality control in a 3D printing system. As will be described, the 3D phantom 100 may include a plurality of positive (i.e., extruding from a surface of the phantom) and negative (i.e., extending inward into a surface of the phantom) topographical features, for example, that may all originate from a common surface of the phantom 100 or multiple surfaces of the phantom 100.

In particular, the phantom 100 includes a support base 104. The support base 104 is illustrated as a rectangular structure extending from a first surface 106 to a second surface 108 that are displaced by a thickness, t. Accordingly, four walls 109, 110, 111, 112 extend along thickness t between the first surface 106 and the second surface 108. A plurality of features 116, 120, 124, 128, 132, 136, 140 are embedded into the first surface 106. The plurality of features 116, 120, 124, 128, 132, 136, 140 embedded into the first surface 106, as will be described, may be negative features.

A plurality of positive features 144, 148, 152, 156, 160, 164 may also be included and protrude from a third surface 166. The third surface 166 may be arranged in a variety of configurations. For example, the third surface 166 may extend to form a common plane with the first surface 106, such that the support base 104 is sufficiently large to support both the first surface 106 and the third surface 166. Furthermore, the third surface 166 and associated positive features 144, 148, 152, 156, 160, 164 may take the place of the second surface 108. Similarly, the third surface 166 and associated positive features 144, 148, 152, 156, 160, 164 may take the place of the first surface 106. Regardless of its particular location of the third surface 166, the positive features 144, 148, 152, 156, 160, 164 may, in some configurations, define a positive feature height substantially equal to the thickness, t. However, the height of the positive features may vary from feature to feature and may have heights much greater or much smaller than thickness t.

The plurality of negative features 116, 120, 124, 128, 132, 136, 140 may include a hollow half sphere 116, a hollow hexagon 120, a hollow rectangle 124, a hollow cone 128, or a plurality of line segment sets 132, 136, 140. The plurality of line segment sets 132, 136, 140 may be arranged in different geometric orientations with respect to one another. In one non-limiting example, the three sets of line segments are arranged along three orthogonal directions in the 3D space, i.e. a first set of line segments 132 is arranged substantially horizontal, a second set of line segments 136 is arranged substantially vertical, and a third set of line segments 140 is arranged along a direction perpendicular to the plane containing the first two sets. In such embodiments, the third set of line segments 140 may have a depth greater than the depth of the first set of line segments 132 and the second set of line segments 136. It should be appreciated, however, that alternative directions are possible as well. Further, each line segment set 132, 136, 140 may further comprise a plurality line segment groups. In one non-limiting example, each of the line segments in a particular line segment group has substantially similar dimensions. Additionally, or alternatively, the depth of the negative features 116, 120, 124, 128, 132, 136, 140 may be designed to be slightly less than or equal to the thickness, t, of the support base 104. However, in some embodiments, the depth of the negative features can vary from feature to feature, or could vary between groups of features. For example, each line segment in the first set of line segments 132 may have a similar depth, while each line segment in the third set of line segments 140 may have a greater depth.

The plurality of positive features 144, 148, 152, 156, 160, 164 may include a solid half sphere 144, a solid hexagon 148, a solid rectangle 152, a solid cone 156, a plurality of cylinders of different diameters 160, a conical shaped feature 164, a combination of these features, or other features that can be 3D printed. The plurality of cylinders of different diameters 160 may be arranged in the form of a vascular tree structure. The conical shaped feature 164 can be shaped in the form of a cochlear structure. As described, the height of the positive features 144, 148, 152, 156, 160, 164 may optionally be designed to match the thickness, t, of the support base 104.

In accordance with one aspect of the present disclosure, the phantom 100 may be constructed from a material selected to facilitate imaging by x-ray-based or other imaging modalities. For example, the phantom 100 may be made of a radiopaque material selected to attenuate x-rays such that the topography of the features on the surfaces 106, 108 of the phantom 100 are distinguishable using x-ray-based imaging modalities, such as fluoroscopy and computed tomography. In other embodiments, the phantom may be produced out of a variety of different polymers, such as high density polyethylene, low density polyethylene, or polycarbonate. Such polymeric materials can provide a similar x-ray attenuation to that of soft tissue, and may better simulate scanning a human body part. The material of the phantom should be chosen such that the phantom provides sufficient contrast in an imaging process and the structures on the phantom can be readily visualized by a number of different imaging processes.

The features 116, 120, 124, 128, 132, 136, 140, 144, 148, 152, 156, 160, 164 in FIG. 2 are designed for quality control assessments. The features 116, 120, 124, 128, 132, 136, 140, 144, 148, 152, 156, 160, 164 and their associated sizes may be selected to test different aspects of a 3D printing system, such as illustrated in FIG. 1. Accuracy, precision, and shape fidelity of 3D printed parts produced are important for patient safety and optimal patient care, and the features of the phantom 100 have been chosen to inspect these qualities, such that proper adjustments to the 3D printing system can be made when unacceptable measurements are observed. The features 116, 120, 124, 128, 132, 136, 140, 144, 148, 152, 156, 160, 164 have been chosen based upon practical considerations, with a preference towards features that provide readily measurable objects, are small in size (therefore decreasing manufacturing time and material cost), and are easy to clean.

In some non-limiting example, the features 116, 120, 124, 128, 132, 136, 140, 144, 148, 152, 156, 160, 164 include both geometric objects and anatomic objects. Examples of geometric objects which may be incorporated by the phantom include but are not limited to line segments 132, 136, 140, hemispheres 116, 144, cones 128, 156 and cubes 124, 152, as well as other such geometric objects. Anatomical objects that may be included in the phantom design include but are not limited to vascular tree structures 160 or cochlear structures 164.

Features chosen for incorporation into the phantom 100 can be varied in size, such that they test different levels of accuracy and precision of the 3D printing system 10. In one configuration, the support base 104 may include several sizes of positive and negative hemispheres 116, 144 and a plurality of sets of differently sized line segments 132, 136, 140. The line segments may be grouped together, such that each line segment in a group has the same dimensions, but every group of line segments is unique relative to other groups of line segments in either width or orientation.

In some embodiments, a phantom 100 may comprise both positive and negative features, as previously described. The number and orientation of positive features may mirror the plurality of negative features, such that the phantom 100 has four positive hemispherical shapes and four negative hemispherical shapes, for example. The orientation of shapes on the phantom may be symmetrical across a center line that divides the support base 104 into two equal surfaces.

To provide rapid qualitative measurement of the printed features, a number of different tests can be used. In some non-limiting examples, a phantom test object can be molded that has the reverse orientation of the printed phantom 100. Accordingly, the test object can have the same positive and negative features as the phantom 100, but can be arranged such that the positive features on the printed phantom 100 align with and can be received within the negative features of the test object. Similarly, the positive features of the test object can be aligned such that they will be received within the negative features of the phantom 100. A qualitative measurement can be taken quickly, in such cases, as a phantom 100 can quickly be determined to fall outside of acceptable tolerances if the objects do not mate together or a surface of the phantom and the test object do not make flush contact with one another. In such embodiments, the phantom test object can operate like a go/no-go gauge.

Other tactics for quick observation can be used to save time in the measurement process as well. Positive features, such as cones, spheres, hexagons, and the like can be produced to test individual negative features of the support base. For example, a plurality of spheres may be printed or injection molded and measured to ensure that they are properly sized to fit within negative features of the phantom 100. Once the phantom 100 is printed, the plurality of spheres may then be placed within a plurality of hemispherical negative features, such as hemispheres 144. If the spheres do not fit properly within a corresponding negative hemisphere 144, an operator can quickly observe that a phantom 100 does not meet the necessary criteria to produce a 3D printed part, and can make adjustments to the 3D printing system. Additionally, inaccuracy of the fit of these parts identifies that error exists within the printing process and machine itself.

Long term stability of the phantom can also be assessed in the above-mentioned method. A comparison of measurements taken at the time of printing and at some other predetermined interval can provide data as to how the part may change over time. Additional physical measurements of the dimensions of the object at any time can be obtained by either high resolution CT imaging or by physically measuring the phantom's dimensions using precision mechanical calipers.

Figure 3:
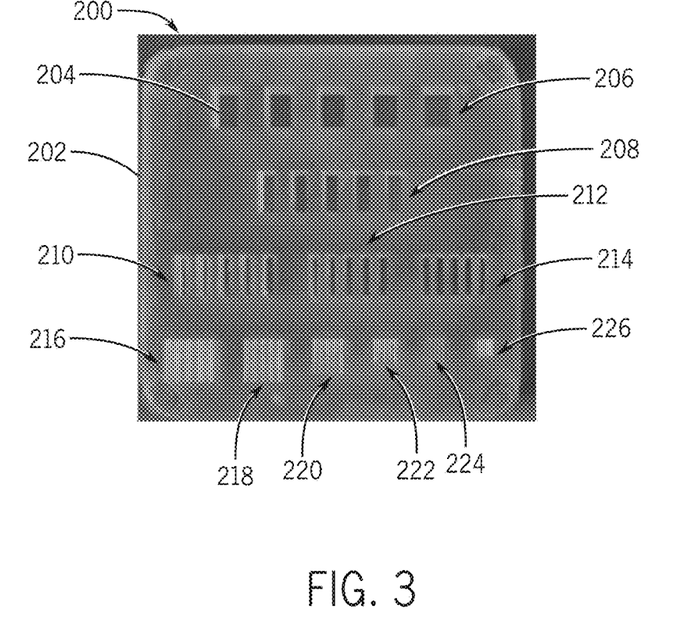
FIG. 3 is an image of another phantom for a 3D printing system in accordance with one aspect of the present disclosure.

Referring to FIG. 3, another phantom 200 for use in a 3D printing quality control method is provided. A perimeter 202 of the phantom 200 is similar to that of a rectangular box, but it should be appreciated that many geometries for the perimeter 202 of the phantom 200 are suitable. While designed for similar use to the phantom 100 of FIG. 2, this phantom 200 may include only negative features. The phantom 200 may include several groups 206, 208, 210, 212, 214, 216, 218, 220, 222, 224, 226 of line segments 204, where each group comprises a selected number of line segments. In one non-limiting example of the invention, the phantom 200 may include eleven groups of line segments 204, and each group may include five individual line segments 204. Each line segment in a group of line segments 206-226 may be dimensioned to be identical, and each group of line segments can have dimensions unique from other groups 206-226 of line segments. In some non-limiting examples, the size of the line segments 204 within each group may define a different size (e.g., the size of the line segments 204 within a group may sequentially become smaller from left to right on the phantom 200). Every line segment 204 in a group can be spaced out evenly with the other line segments in its group 206-226. While each group of line segments 206-226 in FIG. 3 is shown in a vertical orientation, it should be understood that the line segments can be given alternative orientations in the phantom design 200 of the present disclosure. Similarly, while the phantom 200 has been described as only having negative features, it should be understood that the material between these features acts like positive features, and accordingly, the phantom can be considered to include both positive and negative features. Additionally, the phantom 200 can contain a number of other positive features, such as those described with reference to phantom 100, if desired.

Additionally, it should be noted that the phantom 200 of FIG. 3 has not been produced by a 3D printer. The phantom 200 of FIG. 3 is a reference phantom, which may be created by injection molding or other processes capable of producing an object having the necessary surface finish and dimensional accuracy required to use as a reference object. However, the geometry of the phantom 200 is designed such that a 3D printer is capable of producing the features present on the phantom.

Both phantoms 100, 200 provide the ability to evaluate material stability in response to environmental factors (temperature, pressure, humidity) as well as the temporal stability of the materials used to create the models. In some cases, it may be advantageous to both print either model or a variant thereof at a fixed frequency (i.e. monthly or quarterly) and perform routine testing of the phantom by either physically measuring the object or by more sophisticated methods involving imaging and computer analysis. Data from these measurements can be recorded and analyzed to provide information regarding the long term stability of the printed materials and what factors impact the accuracy of the models. The data may also provide information on whether or not the 3D printer requires calibration or maintenance.

Figure 4:
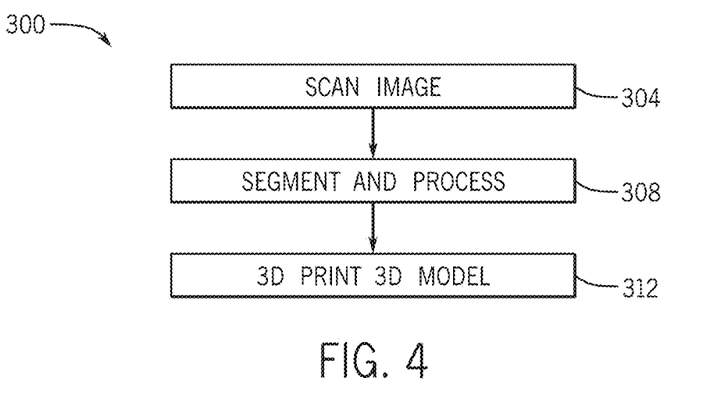
FIG. 4 is a flowchart setting forth an example of steps of a 3D printing process used to produce parts in accordance with one aspect of the present disclosure.

Referring to FIG. 4, a flow chart illustrates a process of 3D printing in medical applications 300. The process 300, at its highest level, includes scanning an item 304 to produce images of the object. These images are then optionally segmented 308. After segmenting the images, they can be imported to modeling software, where they are then reconstructed into a 3D model of the desired part. After the model is reconstructed, this information is transferred to the 3D printer, where the part is outputted 312.

This process 300 can similarly be used to perform a quality control assessment of the entire system. In order to assess the total accuracy of the entire 3D printing procedure, a 3D reference phantom, similar to that of FIG. 2 and FIG. 3, can be imaged using, for example, a CT scanner or another imaging system capable of high resolution scanning. It should be appreciated that other phantoms besides those disclosed by FIG. 2 and FIG. 3 can be used in the system. The 3D reference phantom is then scanned 304 on the scanning system. These images can then be segmented 308 and then imported into modeling software, where the segmented images can be used to reconstruct a 3D model of the phantom. The 3D model of the 3D reference phantom is then transferred to the 3D printer, where the model of the 3D reference phantom is printed 312. Upon completion of the printing process, the features of the 3D printed phantom and the 3D reference phantom can be measured, either manually (i.e. with a caliper or protractor), or by using a high resolution imaging device such as microCT, CT, radiography, or optical imaging, and comparing the scans using a program such as 3-Matic, by Materialise. The distances between the original model and the scanned model can then be calculated on a point by point basis and can be color coded based upon measurement agreement, to provide easy identification of areas of the part that deviate furthest from the desired dimensions. This analysis can also output statistical information regarding the distance distribution of the parts, such as the minimum, maximum, mean, and standard deviation of dimensions in the parts. Based upon the agreement between measurements, a user can determine whether a system is properly calibrated to produce acceptable parts. In order to perform some embodiments of the disclosed process, certain criteria may be advantageously followed, and it is likely that multiple users will be involved. Surgeons or physicians may order the model, given their direct knowledge about the clinical need and there status as end user of the model. Interpreting radiologists possessing expertise in regards to determining optimal imaging study for the given diagnostic question to be addressed by the model may be involved in the process. Medical physicists who understand the imaging physics and technology can ensure exams are performed correctly and may optimize the scanning and reconstruction techniques. Technologists and engineers may perform the imaging, segmentation, and printing of a model. All scanning and reconstruction techniques may be optimized to meet the needs of the associated 3D modeling software. All imaging equipment used in this process may be accredited by the American College of Radiology (ACR) or other accreditation organizations, and may be routinely tested to meet requirements of accreditation and regulation. The images may be segmented using FDA approved software (e.g. Mimics by Materialise), and the segmentation and modeling processes may be performed by experienced technologists and radiologists. Annual maintenance of the 3D printer may be performed by a technician affiliated with the printer manufacturer. Finally, periodic maintenance may be performed on the printer. After each part build, the head and wipers of the 3D printer may be cleaned, a pattern test may be occasionally run to ensure that heads are not getting clogged, and finally, UV lamps may be used to calibrate the system from time to time.

While the steps provided above will help eliminate some error in the 3D printing process, it is recommended that the quality control assessment described above is performed periodically, such as on a weekly basis. Additionally, the test may be performed after any major upgrade to the system, whether the upgrade concerns the software or hardware of any component in the system.

It should also be appreciated that quality control assessment may be performed on just individual components. For example, a quality control assessment could take place that is directed towards just the printing process. In such scenarios, steps 304 scanning an image and 308 segmenting and processing the images could be omitted entirely. A 3D model could instead be produced entirely by design, in CAD, for example. The 3D model could then be 3D printed on a 3D printer 312. The 3D printed part can then be measured in similar ways to those described above, and compared to the measurements of the 3D model. The agreement between measurements would provide feedback on how accurate the printing process is in isolation, and could alert a user that adjustments are necessary in just the printing phase of the process 300.

Figure 5:
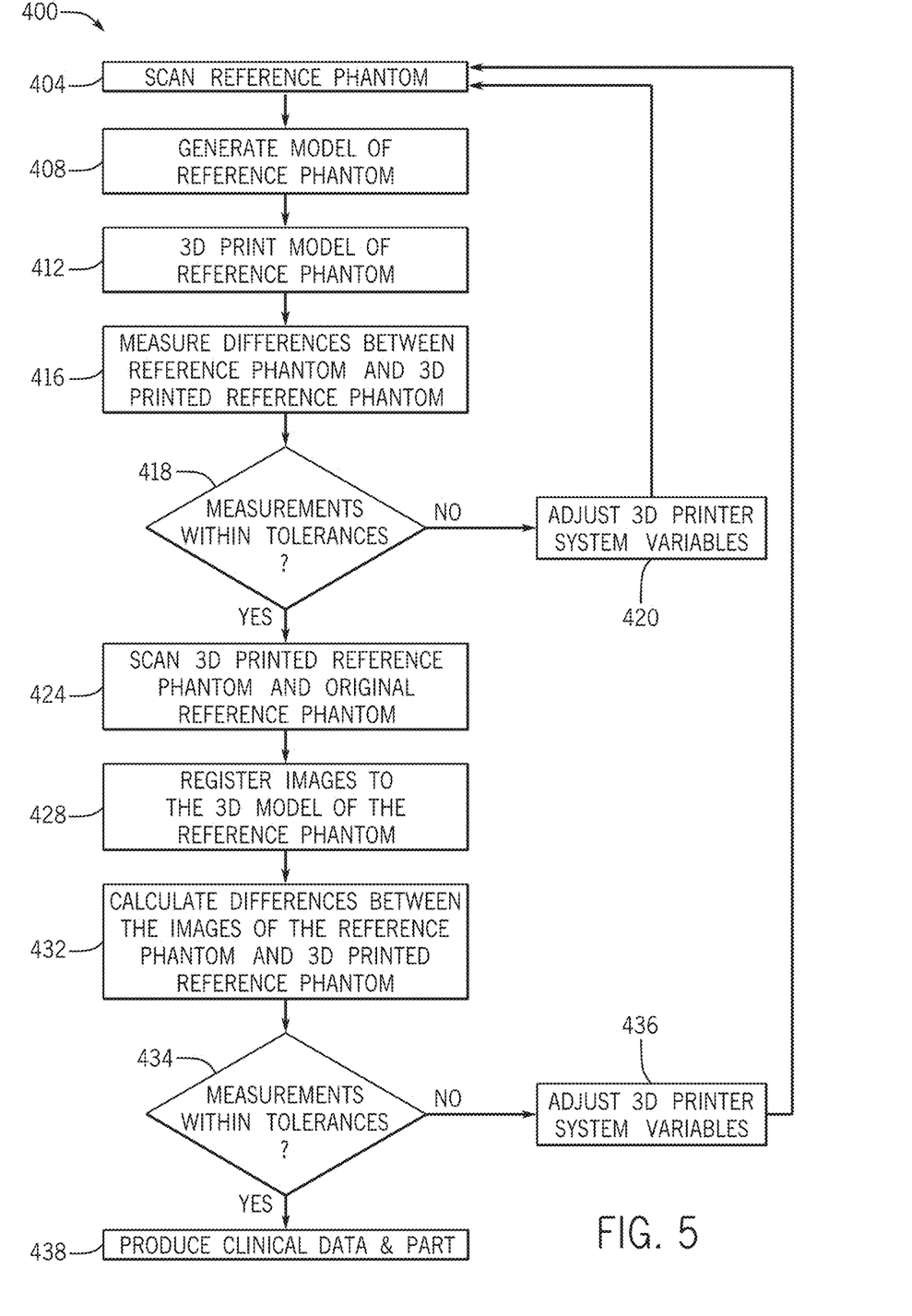
FIG. 5 is a flowchart setting forth an example of steps of a quality control process for a 3D printing system using a reference phantom in accordance with one aspect of the present disclosure.

Referring to FIG. 5, a flow chart is provided that sets forth an example of some steps in a quality control process 400 which can be used to identify and eliminate potential errors at each individual step of the 3D printing process 300, and in doing so, help eliminate the production of unacceptable parts. The process can be performed using a 3D reference phantom, such as the phantoms 100, 200 described with respect to FIG. 2 and FIG. 3.

In some embodiments of the disclosed method of quality control in 3D printed parts for medical applications, a 3D reference phantom is scanned 404 under a scanning device. One such acceptable scanning device is a CT scanner. It should be understood that imaging techniques can influence the 3D printed parts produced by the system, and as such, the imaging technique for scanning the 3D reference phantom should be chosen based on the type of imaging that will be used to scan the patient. By employing common scanning techniques for both the phantom and the patient scan, the imaging system can then also be included in the quality control process, which may be preferable. Although using a system configured for bone scans (which use a high resolution kernel) may produce higher resolution images than a system designed for body imaging (which use a low resolution kernel), if a body imaging tactic will be used to scan a patient, the reference phantom should still be scanned by the system designed for body imaging.

The images obtained from the scanning device can then segmented, processed, and imported into the modeling software. A model of the 3D reference phantom can be generated 408 in the modeling software. Once again, many different types of modeling software are acceptable to accomplish the task of creating a 3D model, including UGS NX 8.0, Mimics, or 3-Matic, for example. Also, the method of segmentation and processing can affect the resolution of a model, as in some cases, segmentation performed without wrapping created a much higher degree of geometric accuracy and resolution for smaller items on the phantom. Excessive wrapping can cause a loss of detail and inaccurate representation of anatomic size in various features.

The information from the 3D model may then be transferred to the 3D printer, where the 3D model of the reference phantom can be printed 412. Many different models of 3D printers may be used to accomplish the printing of this part, including the MakerBot Replicator II Printer. Similarly, different 3D printing processes can be used to print the 3D model of the reference phantom, including SLS. A polymeric material having attenuation qualities similar to the portion of the body being scanned can be used. For example, polymeric materials might include polyethylene, polycarbonate, or other 3D printable polymers. Such polymeric materials can provide a similar x-ray attenuation to that of soft tissue, and may better simulate scanning a human body part. The material of the phantom should be chosen such that the phantom provides sufficient contrast in an imaging process and the structures on the phantom can be readily visualized by a number of different imaging processes.

Once the 3D model has been printed by the 3D printer, a caliper or other measurement technique can be used to measure 416 the features on both the 3D printed reference phantom and the original 3D reference phantom. The measurements are then assessed 418. Agreement between the measurements of these two objects suggests that the entire system is properly calibrated, and can be used to produce acceptable parts for use in medical applications. If agreement between the objects falls outside of a predetermined acceptable tolerance for the parts, the system may be adjusted 420 before attempting to produce any parts that could be used in a medical application.

To further ensure that a quality part will be outputted by the system, additional inspection may be performed. The 3D reference phantom and the 3D printed model of the reference phantom may then be scanned 424 under a high-resolution imaging device. Once again, image quality and imaging techniques can be chosen based upon the desired geometric accuracy and spatial resolution for a given part.

The scanned images of the 3D reference phantom and the 3D printed model of the reference phantom are then registered 428 to the 3D model used to produce the 3D printed reference phantom. Overlaying these images with the model provides valuable data to determine where error may exist in several different areas of the process.

Differences between the registered images and the segmented model can then be calculated 432. Using this data set, differences can be identified between the original 3D reference phantom and the model of the 3D reference phantom, which was created based upon the scanned images of the reference phantom. The assessment of differences may be performed manually or the original 3D reference phantom and the model of the 3D reference phantom may be imaged and assessed using automated processes. Similarly, a combination of user assessment and software assessment may be used to calculate differences between the parts.

Regardless of the particular implementation of the assessment, assessing the original 3D reference phantom and the model of the 3D reference phantom identifies whether any, and to what extent, errors existed during the modeling phase of the 3D printing process, or whether errors were incurred by printing the part. Differences between the 3D model and the 3D printed part isolate the data such that the error specifically associated with just the modeling process or just the printing process can be observed. Finally, comparison between the images of the 3D reference phantom and the 3D printed model of the reference phantom can be used to check the total error associated with the process 400. Calculating on a point-by-point basis, the final error associated with the entire system can be calculated.

These measurements are then compared to desired tolerances 434. If a part meets the tolerances associated with each phase of the 3D printing process, the production of a clinical data set can begin 438, as will be described with respect to FIG. 6. If values outside of a predetermined tolerance are observed, the printer system must be adjusted 436 to compensate for these deficiencies, and the test 400 must start over.

Figure 6:
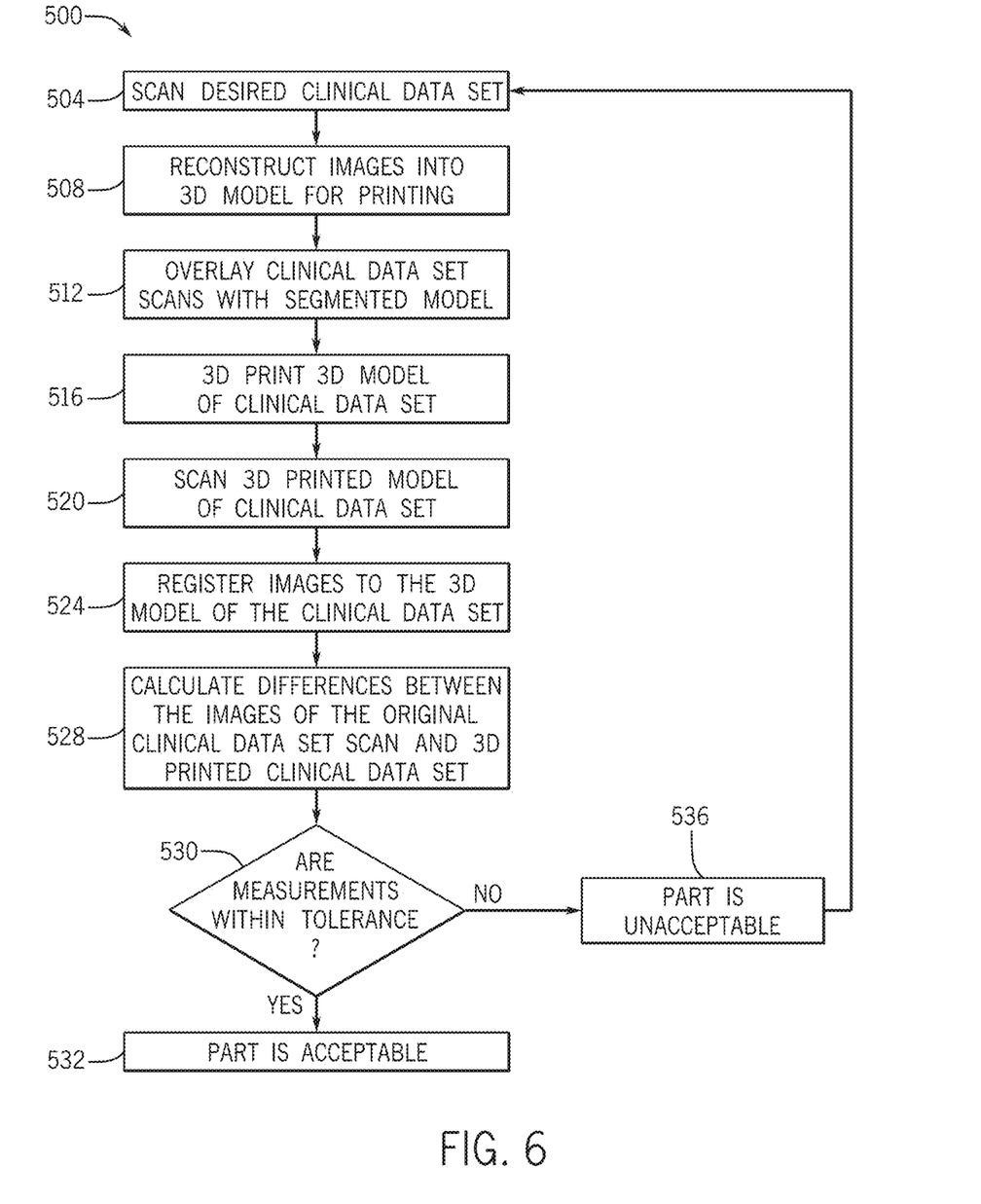
FIG. 6 is a flowchart setting forth an example of steps of a quality control process for a 3D printing system used to produce a clinical model in accordance with one aspect of the present disclosure.

Referring to FIG. 6, a method of quality control for 3D printing a clinical data set 500 is shown. In one non-limiting example, the parts being produced may include a radial-ulna set. The process can begin by scanning a desired clinical data set 504, obtaining 3D volumetric images of the patient having the anatomy of interest using a scanning device, such as a CT scanner or MRI. The quality of the input image data directly affects the quality of the final model, so imaging criteria such as spatial resolution and signal-to-noise ratio could be chosen to produce the best image reasonably obtainable. Thorough control of the image quality plays an important role in anatomical modeling, and imaging techniques that can produce high quality images are preferred.

For any imaging system, there are multiple scanning and reconstruction parameters that directly affect image quality. Accordingly, the scanning protocol should be optimized to meet the needs of 3D modeling. For example, to get an acceptable model of vascular structures, bolus timing can be adjusted to separate the arterial and venous phase of the contrast enhancement. Lower tube potential (kV) can be used to increase the enhancement of iodine contrast in the vascular trees. Slice thickness and reconstruction kernel play an important role in image quality as well. Images with thick slices may generate discontinuous, stair-well like boundaries on the printed model. Reconstruction kernel impacts both image resolution and image noise, which need to be balanced based upon the applications. For models with fine details, such as temporal bone models, for example, a sharp kernel is more appropriate to get the best spatial resolution. For models with large size having low contrast objects, such as a liver lesion, a smooth kernel is more appropriate to control image noise.

Different imaging techniques can be adopted to assist the process of modeling which improve the accuracy of the final model. In regular CT images, both bone and iodine enhanced vessels have high CT numbers and appear to be bright. As such, it could be a challenge to separate bones and vessels. In such cases, dual energy CT using the energy dependence of attenuation coefficient can easily differentiate these two materials. In this case, a bone removal process can be performed to remove bones while leaving iodine enhanced vessels. Similar imaging techniques may be employed when metal artifact affects image quality.

The scans taken of the particular body part(s) are then optionally segmented and can be imported into modeling software, such as UGS NX 8.0, Mimics, or 3-Matic, where they can be reconstructed 508 into a 3D model suitable for printing. In order to ensure that the 3D model accurately represents the clinical data set, the original scans of the clinical data set may be overlaid 512 with the segmented model. Using these images and the model, the agreement between the 3D model and the scans can be assessed in all three planes, and the processes repeated or the model adjusted such that optimal agreement between the two can be achieved.

Once agreement between the segmented model and the original clinical data set scans has been confirmed, the 3D model can be outputted as a stereolithography (STL) file, sent to the printer, and printed 516 on a 3D printer, such as the MakerBot Replicator II Printer or a different model. Again, a number of different printing processes, such as SLS, can be used in the printing of a desired clinical data set part. After printing, the printer head and wiper may be cleaned to prevent clogging. UV lamp calibration can also be performed periodically as well, to ensure that parts are properly produced in the printer. Any additional routine maintenance for the printer should be performed as necessary. Preventative maintenance may also be performed by a technician after a certain period of time, such as every 3500 print hours. Worn plates and tubing may be replaced and in-depth factory level calibrations and tests can be performed to ensure the printer is functioning optimally.

After the model has been printed, it can be cleaned to remove supporting materials. Because poor cleaning could affect the image quality, care should be taken to ensure that all residual materials have been removed without removing any structures of the model. Residual material may be removed in a number of different ways. In some embodiments, the part can be cleaned by spraying a water or alcohol-based solution over the finished part. A visual check may be performed to double check the model is what it is intended to be. For models involving hollow spaces, such as vascular models, special care should be taken to ensure that residual matter has been removed. A CT scan can easily reveal the internal structure of the vessel and whether there are residual supporting materials remaining inside. Additionally, material property can be checked. In some examples, different materials may produce different image qualities. In one experiment, the same trachea model printed with two different materials (one rigid, one soft) showed a different inner lumen of the vessel. Material integrity may play an important role for models if they are kept for a long time. In some models produced by the disclosed method, cracks and deformation occurred after the models were left on the shelf for over a year. Accordingly, a recheck of model integrity should be performed if the models are used a long time after they are built.

Using a high-resolution scanner, such as a CT scanner, the 3D printed model of the clinical data set can then be scanned 520. The scans of the 3D printed model may then be registered 524 to the 3D model of the clinical data set in the 3D modeling software. Using these images, the differences between the 3D printed clinical data set and the 3D model of the clinical data set can be calculated 528 on a point-by-point basis. These measurements can then be compared to tolerances 530 to determine whether a printed part is acceptable for a desired medical application. If measurements fall outside of predetermined tolerances, the part can be discarded 536 or adjusted appropriately to meet a desired specification for the clinical data set. If the part is acceptable, the part may be used for its intended purpose 532.

Figure 7A:
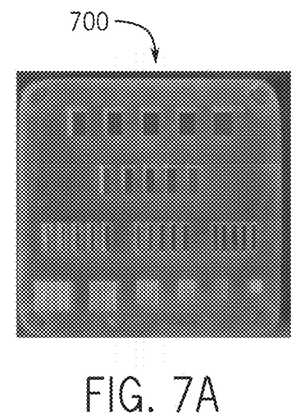
FIG. 7A is an image of the reference phantom of FIG. 3.
Figure 7B:
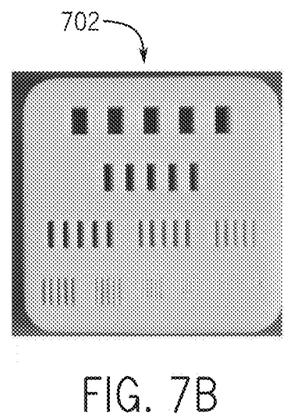
FIG. 7B is an image of a printed version of the reference phantom of FIG. 7A printed with a 3D printing system in accordance with one aspect of the present disclosure.
Figure 7C:
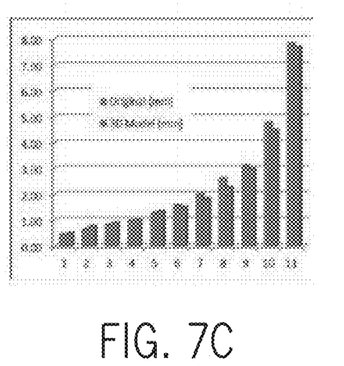
FIG. 7C is a graph illustrating a geometric comparison between the reference phantom of FIG. 7A and the printed version of the reference phantom of FIG. 7B.

Referring to FIGS. 7A-7C, a comparison of a 3D reference phantom and a 3D printed model of that 3D reference phantom is provided. FIG. 7A shows a 3D reference phantom 700 produced by injection molding or other processes. Using the method of FIG. 4, the 3D reference phantom 700 was scanned under a high resolution imaging device. Using the images obtained from the scan, a 3D model of the 3D reference phantom was created. Using this 3D model, a 3D printed model 702 illustrated in FIG. 7B was printed by a 3D printer. Using a caliper, measurements of the dimensions of the line groups were compared and mapped in FIG. 7C to determine the quality of the entire printing process. The agreement or disagreement of the measurements can demonstrate the influence of imaging technique (reconstruction kernel) and processing technique (wrapping) on the model accuracy.

Figure 8A:
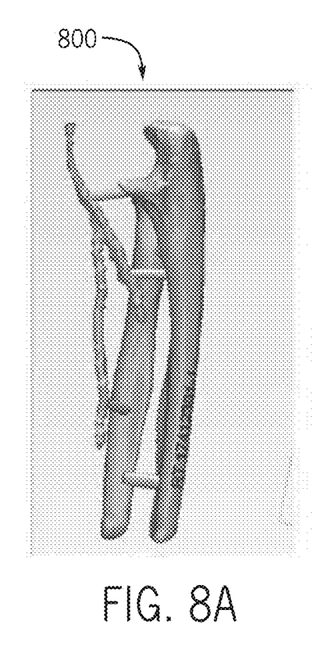
FIG. 8A is an image of a 3D model of a portion of human anatomy.
Figure 8B:
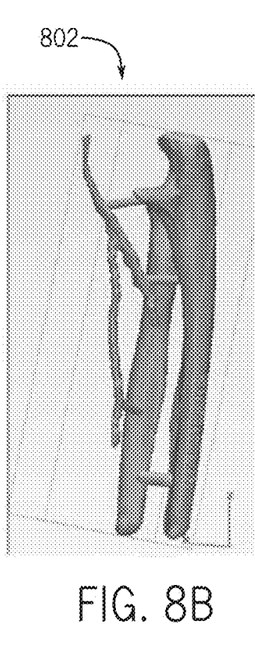
FIG. 8B an image of a printed version of the portion of human anatomy of FIG. 8A printed with a 3D printing system.
Figure 8C:
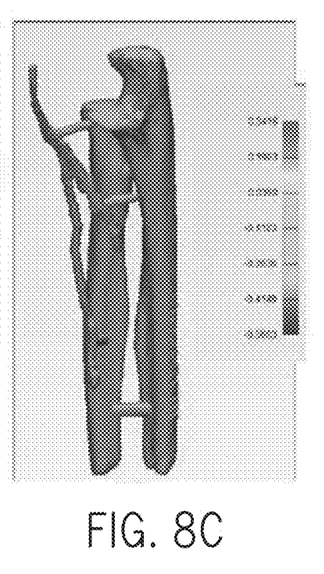
FIG. 8C is a graphic illustrating a geometric comparison between the 3D model of the portion of human anatomy of FIG. 8A and the printed version of the portion of human anatomy of FIG. 8B.

Referring to FIGS. 8A-8C, a comparison of clinical data sets is provided. The method of FIG. 6 was followed, in that an original patient scan was taken by a scanning device capable of scanning a desired portion of the body. The images were then segmented and imported into 3D modeling software, where the images were reconstructed into a 3D model 800. Agreement between the patient scan and the 3D model was checked in all 3 planes. FIG. 8A shows a 3D model 800 that represented the final 3D model of the clinical data set that was sent to a 3D printer, where it was printed. The printed 3D model of the clinical data 802 set was scanned under a high resolution scanning device and is illustrated in FIG. 8B. The images of the device were transferred to the modeling software, where the scans of the 3D printed clinical data 802 set were compared to the dimensions of the 3D model 800. The two data sets were then compared, as illustrated in FIG. 8C, and the differences in measurement between the items were determined on a point-by-point basis.

Figure 9:
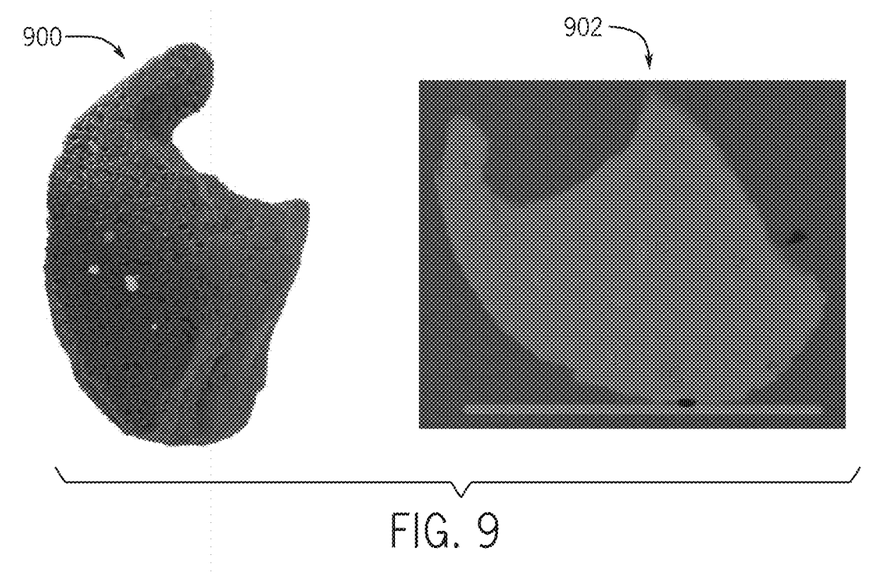
FIG. 9 is an image of an example of a patient-specific 3D printed phantom of a liver with its associated CT scan.

Referring to FIG. 9, a patient-specific, attenuation correct liver phantom 900 has been created, and the associated CT image of the phantom 902 is provided. Because it is not compliant with radiation dose standards nor cost-effective to repeatedly scan patients under a CT scanner, a patient-specific 3D printed phantom 900 that has the appropriate dimensions can serve as a useful tool in medical applications. A 3D printed patient-specific phantom 900 can be used to prepare for difficult procedures, allowing a surgeon to practice on a dimensionally correct item before performing a task.

After the part is produced, physical measurements to the anatomic model can be performed. In some examples, the distance between landmarks can be measured with a caliper, and angles can be measured with a protractor. However, these measurements are sometimes limited, and it may be more appropriate to use imaging techniques to assist the validation of the models. The printed model can be scanned using a high resolution imaging modality to avoid additional errors. The images can be imported into modeling software, segmented out, and built into a virtual model. The model can then be registered to the segmented model from the patient images. After registration, the agreement between the two images can be analyzed. The distance between the original model and the scanned model can be calculated on a point by point basis and color coded to provide easy identification of points of maximum agreement and disagreement.

For phantoms built as flexible models, the measurement phase could be difficult to perform. Once the models are constructed, they may deform. To ensure the model maintains original positioning during the scan, it may be helpful to build some supporting structures while building the model at the original position it would be in a patient. This way, the method can still be used.

To ensure that a 3D printed anatomic model is properly used and identifiable, each 3D printed anatomic model can be labeled with a unique identifier for traceability. In some examples, the part may be labeled with a patient last name or a clinic number. Additionally, other identifiers may be necessary to mark left or right extremities, or mirror imaged anatomy. All labels are imprinted on anatomic models through a computer aided design program.

Figure 10:
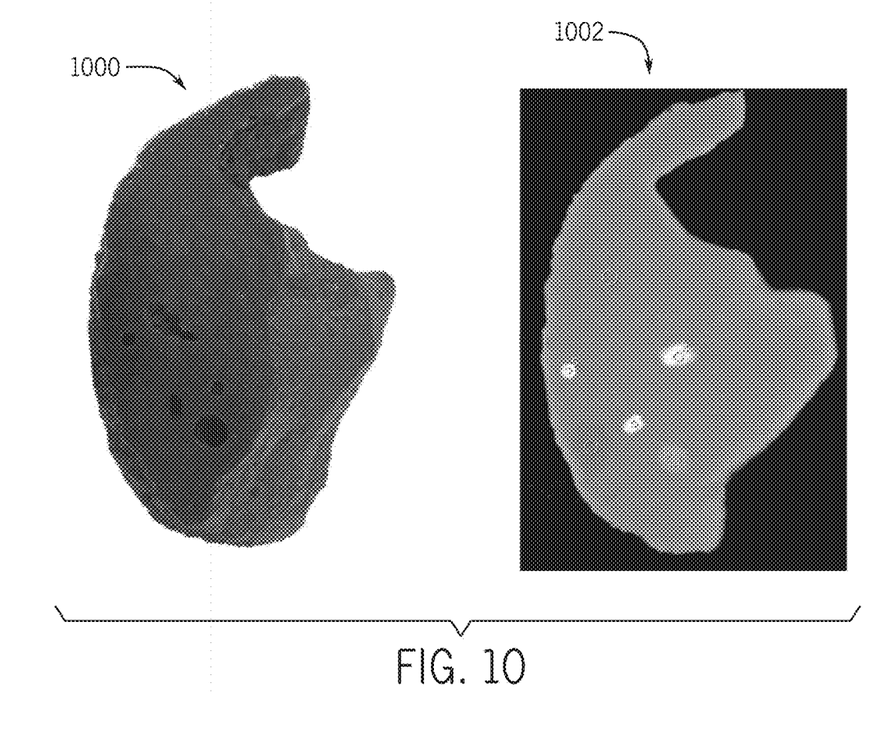
FIG. 10 is an image of an example of a patient-specific 3D printed phantom and its associated CT scan where an iodine solution has been placed into vessels in the phantom and a concentration has been adjusted to mimic different levels of concentration in an actual patient liver.

Referring to FIG. 10, a patient-specific, attenuation correct liver phantom 1000 has been created as a hollow vessel, and is shown alongside its associated CT scan 1002. Using iodine solutions of variable concentrations, the phantom 1000 can be used to mimic different levels of vessel enhancement. Using the phantom 1000 to mimic the levels of vessel enhancement present in the specific patient that the phantom was associated with can be used to determine the lowest dose of radiation that can be used without sacrificing the diagnosis. Allowing the reduction of radiation dose to a patient promotes patient safety, while allowing medical personnel to plan treatment programs for specific patients.

Additional applications of patient-specific 3D printed phantom production include the creation of patient-specific bolus for use in modulated electron radiation therapy. Using 3D printed boluses, medical personnel can determine required doses for use in radiation therapy, particularly proton therapy, intensity modulated radiation therapy (IMRT), and radiosurgery, among others. Determining proper dosage can save patients from potentially experiencing excessive harmful radiation, again promoting patient safety while reducing costs of treatment.

The use of patient specific 3D phantoms can also be used as a quality assurance tool for procedures that require high accuracy to perform, such as those of proton therapy, intensity modulated radiation therapy (IMRT), radiosurgery, and the like. The use of a phantom allows the system to perform a procedure multiple times on an object without the risk of harm to a patient. Using a 3D printed patient-specific phantom can allow medical personnel to perform a complicated procedure once without the risk of harming a patient. In doing so, patient safety is further promoted, as the medical personnel have more experience, and also can verify that a machine is properly calibrated to perform the desired task.

Thus, the present invention discloses methods of checking the part at each phase of the printing process, and in doing so, ensures that an acceptable part is produced by the 3D printing system.

Thus, while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A method of quality control for a 3D printing system, the method comprising:
    scanning a 3D reference phantom with a scanning device thereby producing one or more scanned images of the 3D reference phantom;
    importing the one or more scanned images into modeling software;
    generating a 3D model of the 3D reference phantom in the modeling software;
    printing a printed 3D phantom on a 3D printer in communication with the modeling software;
    comparing a size of at least one geometric feature of the printed 3D phantom to a size of a corresponding at least one geometric feature of the 3D reference phantom; and
    upon comparing the size of the at least one geometric feature of the printed 3D phantom to the size of the corresponding at least one geometric feature of the 3D reference phantom, determining at least one of a geometric accuracy, a resolution, and a shape fidelity of the 3D printing system.

2. The method of claim 1, wherein the 3D reference phantom comprises a plurality of line-pair groups.

3. The method of claim 2, wherein the plurality of line-pair groups include different sized openings.

4. The method of claim 1, wherein the scanning device is at least one of a CT scanner, a microCT scanner, an optical imager, and an x-ray machine.

5. The method of claim 1, wherein comparing the size of the at least one geometric feature of the printed 3D phantom to the size of the corresponding at least one geometric feature of the 3D reference phantom comprises imaging the printed 3D phantom and the 3D reference phantom; and
    creating a visual map illustrating measured differences between the printed 3D phantom and the 3D reference phantom.

6. The method of claim 5, wherein the imaging equipment is a CT scanner, microCT scanner, optical imager, or an x-ray machine.

7. The method of claim 1, wherein comparing the size of the at least one geometric feature of the printed 3D phantom to the size of the corresponding at least one geometric feature of the 3D reference phantom comprises manually measuring the size of the at least one geometric feature of the printed 3D phantom and the size of the corresponding at least one geometric feature of the 3D reference phantom.

8. A method of producing a patient-specific part using a 3D printing system, the method comprising:
   scanning a portion of a patient's body with a scanning device thereby producing one or more images of the portion of the patient's body;
   importing the one or more images into modeling software;
   segmenting the one or more images to form a segmented set of images;
   generating a 3D model of the portion of the patient's body from the segmented set of images;
   printing, with a 3D printer, a printed 3D model of the portion of the patient's body;
   scanning the printed 3D model of the portion of the patient's body with the scanning device thereby producing one or more images of the printed 3D model;
   registering the one or more images of the printed 3D model to the 3D model in the modeling software;
   calculating a geometric difference between the one or more images of the printed 3D model and the 3D model in the modeling software on a point-by-point basis; and
   determining if the calculated geometric difference between the one or more images of the printed 3D model and the 3D model in the modeling software are within a pre-determined tolerance.

9. The method of claim 8, wherein the scanning device is at least one of a CT scanner, a microCT scanner, an optical imager, and an x-ray machine.

10. The method of claim 8, wherein the step of printing the 3D model of the portion of the patient's body includes adding patient-identifying information to the printed 3D model.

11. The method of claim 8, wherein the method further comprises cleaning a portion of the 3D printed model with a liquid.

12. The method of claim 8, wherein the step of calculating the geometric difference between the one or more images of the printed 3D model and the 3D model in the modeling software is performed by overlaying the segmented set of images with the scans from the printed 3D model.

13. The method of claim 8, wherein the method comprises testing the accuracy of the printer by comparing the one or more images of the 3D printed model to the 3D model in the modeling software and comparing the images on a point by point basis.

* * * * *